US007851674B2

(12) United States Patent
Davies et al.

(10) Patent No.: US 7,851,674 B2
(45) Date of Patent: Dec. 14, 2010

(54) GENERATION OF PLANTS WITH ALTERED OIL, PROTEIN, OR FIBER CONTENT

(75) Inventors: John P. Davies, Portland, OR (US); Hein Tsoeng (Medard) Ng, Charlottesville, VA (US)

(73) Assignee: Agrinomics LLC, Portland, OR (US)

( * ) Notice: Subject to any disclaimer, the term of this patent is extended or adjusted under 35 U.S.C. 154(b) by 242 days.

(21) Appl. No.: 11/956,220

(22) Filed: Dec. 13, 2007

(65) Prior Publication Data

US 2008/0160160 A1 Jul. 3, 2008

Related U.S. Application Data

(60) Provisional application No. 60/870,357, filed on Dec. 15, 2006.

(51) Int. Cl.
*A01H 1/06* (2006.01)
*C12N 15/01* (2006.01)
*C07H 21/04* (2006.01)

(52) U.S. Cl. .................... 800/281; 800/278; 800/295; 800/298; 435/6; 435/441; 536/24.3; 536/23.6

(58) Field of Classification Search .................... None
See application file for complete search history.

(56) References Cited

U.S. PATENT DOCUMENTS

| 5,322,783 | A | 6/1994 | Tomes et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,610,042 | A | 3/1997 | Chang et al. |
| 5,639,790 | A | 6/1997 | Voelker et al. |
| 5,704,160 | A | 1/1998 | Bergquist et al. |
| 5,952,544 | A | 9/1999 | Browse et al. |
| 6,229,033 | B1 | 5/2001 | Knowlton |
| 6,248,939 | B1 | 6/2001 | Leto et al. |
| 7,528,295 | B2 * | 5/2009 | Lightner et al. ............ 800/298 |
| 2004/0025202 | A1 | 2/2004 | Laurie et al. |
| 2006/0048240 | A1 | 3/2006 | Alexandrov et al. |
| 2006/0150283 | A1 | 7/2006 | Alexandrov et al. |
| 2006/0277630 | A1 | 12/2006 | Lightner et al. |

FOREIGN PATENT DOCUMENTS

| EP | 1033405 | 9/2000 |
| WO | WO 94/11516 | 5/1994 |
| WO | WO 95/06128 | 3/1995 |
| WO | WO 02/072775 | 9/2002 |
| WO | WO 2004/092367 | 10/2004 |
| WO | WO 2004/093528 | 11/2004 |
| WO | WO 2004/093532 | 11/2004 |
| WO | WO 2005/107437 | 11/2005 |
| WO | WO 2006/007432 | 1/2006 |
| WO | WO 2007/053482 | 5/2007 |
| WO | WO 2008/034648 | 3/2008 |

OTHER PUBLICATIONS

Database UniProt, Accession No. Q9LK50, Jun. 27, 2006.*
Anoop et al., "Modulation of citrate metabolism alters aluminum tolerance in yeast and transgenic canola overexpressing a mitochondrial citrate synthase," *Plant Physiol.* 132, 2205-2217 (2003).
Bateman et al., "Pfam 3.1: 1313 multiple alignments and profile HMMs match the majority of proteins," *Nucleic Acids Res.*, 27:260-262, 1999.
Beisson, et al., "*Arabidopsis* genes involved in acyl lipid metabolism. A 2003 census of the candidates, a study of the distribution of expressed sequence tags in organs, and a web-based database," *Plant Physiol.*, 132:681-697 (2003).
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, (2003).
Browse et al., "Fluxes through the prokaryotic and eukaryotic pathways of lipid synthesis in the '16:3' plant *Arabidopsis thaliana*," *Biochem J.* 235:25-31 (1986).
Chapple and Carpita, "Plant cell walls as targets for biotechnology," *Current Opinion in Plant Biology*, 1:179-185 (1998).
Christensen et al., 9th *International Conference on Arabidopsis Research*, Univ. of Wisconsin-Madison, Jun. 24-28, Abstract 165 (1998).
Christou et al., "Inheritance and expression of foreign genes in transgenic soybean plants," *Proc. Natl. Acad. Sci. USA*, 86:7500-7504 (1989).
Colbert et al., "High-throughput screening for induced point mutations," *Plant Physiol.* 126:480-484 (2001).
De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).
Dehesh et al., "Overexpression of 3-ketoacyl-acyl-carrier protein synthase IIIs in plants reduces the rate of lipid synthesis," *Plant Physiol.*, 125:1103-1114 (2001).
Douglas et al., "Nutritional evaluation of low phytate and high protein corns," *Poultry Sci.* 79:1586-1591 (2000).
Eastmond et al., "Re-examining the role of the glyoxylate cycle in oilseeds," *Trends Plant Sci.*, 6:72-78 (2001).
Eccleston et al., "Expression of lauroyl-acyl carrier protein thioesterase in *Brassica napus* seeds induces pathways for both fatty acid oxidation and biosynthesis and implies a set point for triacylglycerol accumulation," *Plant Cell.* 10:613-622 (1998).
Edwards et al., "Protein and energy evaluation of soybean meals processed from genetically modified high-protein soybeans," *Poultry Sci.* 79:525-527 (1999).
Everett et al., "Genetic engineering of sunflower (*Helianthus annuus* L.)," *Bio/Technology*, 5:1201 (1987).
Falco et al., "Transgenic canola and soybean seeds with increased lysine," *Bio/Technology*, 13:577-582 (1995).

(Continued)

*Primary Examiner*—Eileen B O Hara
(74) *Attorney, Agent, or Firm*—Klarquist Sparkman, LLP.

(57) ABSTRACT

The present invention is directed to plants that display an improved oil quantity phenotype or an improved meal quality phenotype due to altered expression of an HIO nucleic acid. The invention is further directed to methods of generating plants with an improved oil quantity phenotype or improved meal quality phenotype.

6 Claims, No Drawings

OTHER PUBLICATIONS

Fatland et al., "Molecular biology of cytosolic acetyl-CoA generation," *Biochem Soc Trans.*, 28:593-595 (2000).
Fatland et al., "Reverse genetic characterization of cytosolic acetyl-CoA generation by ATP-citrate lyase in *Arabidopsis*," *Plant Cell.*, 17:182-203 (2004).
Feldmann et al., "A Dwarf Mutant of *Arabidopsis* Generated by T-DNA Insertion Mutagenesis," *Science*, 243:1351-1354 (1989).
Focks et al., "wrinkled1: A novel, low-seed-oil mutant of *Arabidopsis* with a deficiency in the seed-specific regulation of carbohydrate metabolism," *Plant Physiol.*, 118:91-101 (1998).
Fridborg et al., "The *Arabidopsis* dwarf mutant *shi* exhibits reduced gibberellin responses conferred by overexpression of a new putative zinc finger protein," *Plant Cell*, 11:1019-1032 (1999).
Girke et al., "Microarray analysis of developing *Arabidopsis* seeds," *Plant Physiol.* 124:1570-1581 (2000).
Hayashi et al., "Activation of a plant gene by T-DNA tagging: auxin-independent growth in vitro," *Science*, 258:1350-1353 (1992).
Honig and Rackis, "Determination of the total pepsin-pancreatin indigestible content (dietary fiber) of soybean products, wheat bran, and corn bran," *J. Agri. Food Chem.*, 27:1262-1266 (1979).
Jako et al., "Seed-specific over-expression of an *Arabidopsis* cDNA encoding a diacylglycerol acyltransferase enhances seed oil content and seed weight," *Plant Physiol.*, 126(2):861-74 (2001).
James and Dooner, "Isolation of EMS-induced mutants in *Arabidopsis* altered in seed fatty acid composition," *Theor. Appl. Genet.*, 80:241-245 (1990).
Kardailsky et al., "Activation tagging of the floral inducer FT," *Science*, 286:1962-1965 (1999).
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409 (1995).
Katavic et al., "Utility of the *Arabidopsis* FAE1 and yeast SLC1-1 genes for improvements in erucic acid and oil content in rapeseed," *Biochem Soc Trans.*, 28:935-937 (2000).
Kline et al., "High velocity microprojectiles for delivering nucleic acids into living cells," *Nature*, 327:70-73 (1987).
Larson et al., "Acyl CoA profiles of transgenic plants that accumulate medium-chain fatty acids indicate inefficient storage lipid synthesis in developing oilseeds," *Plant J.*, 32:519-527 (2002).
Lemieux et al., "Mutants of *Arabidopsis* with alterations in seed lipid fatty acid composition," *Theor. Appl. Genet.*, 80:234-240 (1990).
Lin et al., "The Pex16p homolog SSE1 and storage organelle formation in *Arabidopsis* seeds," *Science*, 284:328-330 (1999).
Lionneton et al., "Development of an AFLP-based linkage map and localization of QTLs for seed fatty acid content in condiment mustard (*Brassica juncea*)," *Genome*, 45:1203-15 (2002).
Liu et al., "A transcriptional switch in the expression of yeast tricarboxylic acid cycle genes in response to a reduction or loss of respiratory function," *Mol Cell Biol.*, 19:6720-6728 (1999).
McCallum et al., "Targeted screening for induced mutations," *Nature Biotechnology*, 18:455-457 (2000).
Mekhedov et al., "Toward a functional catalog of the plant genome. A survey of genes for lipid biosynthesis," *Plant Physiol.*, 122:389-402 (2000).
Moire et al., "Impact of unusual fatty acid synthesis on futile cycling through beta-oxidation and on gene expression in transgenic plants," *Plant Physiol.*, 134:432-442 (2004).
Moore et al., "Chromatography of Amino Acids on Sulfonated Polystyrene Resins," *Anal. Chem.*, 30:1185-1190 (1958).
Mulder et al., "The InterPro Database, 2003 brings increased coverage and new features," *Nucleic Acids Res.*, 31:315-318, 2003.
Neuhaus et al., "Nonphotosynthetic Metabolism in Plastids," *Annu Rev Plant Physiol Plant Mol Biol.*, 51:111-140 (2000).
O'Hara et al., "Fatty acid and lipid biosynthetic genes are expressed at constant molar ratios but different absolute levels during embryogenesis," *Plant Physiol.*, 129:310-320 (2002).
Okuley et al., "*Arabidopsis FAD2* gene encodes the enzyme that is essential for polyunsaturated lipid synthesis," *Plant Cell*, 6:147-158 (1994).
Parsons et al., "Nutritional evaluation of soybean meals varying in oligosaccharide content," *Poultry Sci.*, 79:1127-1131 (2000).
Pritchard et al., "Germination and storage reserve mobilization are regulated independently in *Arabidopsis*," *Plant J.*, 31:639-647 (2002).
Rangasamy et al., "Genetic enhancement of fatty acid synthesis by targeting rat liver ATP:citrate lyase into plastids of tobacco," *Plant Physiol.*, 122:1231-1238 (2000).
Rangasamy et al., "Compartmentation of ATP:citrate lyase in plants," *Plant Physiol.* 122:1225-1230 (2000).
Ratledge et al., "Correlation of ATP/citrate lyase activity with lipid accumulation in developing seeds of *Brassica napus* L. Lipids," 32:7-12 (1997).
Rawsthorne, "Carbon flux and fatty acid synthesis in plants," *Prog Lipid Res.* 41:182-196 (2002).
Ruuska et al., "Contrapuntal networks of gene expression during *Arabidopsis* seed filling," *Plant Cell.*, 14:1191-1206 (2002).
Comai et al., "Efficient discovery of DNA polymorphisms in natural populations by Ecotilling," *The Plant Journal*, 37:778-786 (2004).
Zou et al., "Modification of Seed Oil Content and Acyl Composition in the Brassicaceae by Expression of a Yeast *sn*-2 Acyltransferase Gene," *The Plant Cell*, 9:909-923 (1997).
Rylott et al., "Co-ordinate regulation of genes involved in storage lipid mobilization in *Arabidopsis thaliana*," *Biochem Soc Trans.*, 29:283-287 (2001).
Schaffer et al., "The late elongated hypocotyl mutation of *Arabidopsis* disrupts circadian rhythms and the photoperiodic control of flowering," *Cell*, 93:1219-1229 (1998).
Schnarrenberger et al., "Evolution of the enzymes of the citric acid cycle and the glyoxylate cycle of higher plants. A case study of endosymbiotic gene transfer," *Eur J Biochem.*, 269:868-883 (2002).
Schnurr et al., "Characterization of an acyl-CoA synthetase from *Arabidopsis thaliana*," *Biochem Soc Trans.*, 28:957-958 (2000).
Shewry, "Seed storage proteins: structures and biosynthesis," *Plant Cell*, 7:945-956 (1995).
Shockey et al., "Characterization of the AMP-binding protein gene family in *Arabidopsis thaliana*: will the real acyl-CoA synthetases please stand up?" *Biochem Soc Trans.*, 28:955-957 (2000).
Thelen et al., "Biotin carboxyl carrier protein isoforms in Brassicaceae oilseeds," *Biochem Soc Trans.*, 28:595-598 (2000).
Weigel et al., "Activation tagging in *Arabidopsis*," *Plant Physiology*, 122:1003-1013 (2000).
White et al., "A new set of *Arabidopsis* expressed sequence tags from developing seeds. The metabolic pathway from carbohydrates to seed oil," *Plant Physiol.*, 124:1582-1594 (2000).
Wilson et al., "A Dissociation insertion causes a semidominant mutation that increases expression of TINY, an *Arabidopsis* gene related to APETALA2," *Plant Cell*, 8:659-671 (1996).
Yadav et al., "Cloning of higher plant omega-3 fatty acid desaturases," *Plant Physiol.*, 103:467-476 (1993).
Database EMBL, Accession No. BT015533, Sep. 4, 2004, 1 page.
Zhao et al., "Conditional QTL mapping of oil content in rapeseed with respect to protein content and traits related to plant development and grain yield," *Theoretical and Applied Genetics*, 113(1): 33-38 (2006).
Zhao et al., "Oil content in a European x Chinese rapeseed population: QTL with additive and epistatic effects and their genotype-environment interactions," *Crop Science*, 45(1): 51-59 (2005).

\* cited by examiner

SEQUENCE LISTING

<160> NUMBER OF SEQ ID NOS: 8

<210> SEQ ID NO 1
<211> LENGTH: 936
<212> TYPE: DNA
<213> ORGANISM: Arabidopsis thaliana

<400> SEQUENCE: 1

```
atggatacag gaaataacaa taatcttccc actcttctaa agtgtaactt tcctccatat      60
ggaaaagatt atcctggagg cttcgctact ggaagatttt ctgatggaag agttccttct     120
gatcttattg cggaaaagtt gggattggct aagacattac cagcatatat gaatccgtat     180
ttgaagccag aggatcttct taaaggtgta acatttgcat ctggaggaac tggttatgat     240
ccattgacag caaaaattat gtcagtaata tcggtgtggg atcaactcat aaatttcaaa     300
gaatatatat caaagatcaa gaggcatttc ggagaagaaa aagccaaaga tatcttggaa     360 catagttttct ttcttgtggt gtctagtagc aatgaccttg ctcacactta tttagctcaa     420
actcatcgat atgatcgtac ctcttatgcc aatttcttgg ctgactctgc tgtccatttc     480
```

-continued

```
gtgagagaat tacataagct tggagctcgg aaaataggag tgtttagtgc agtcccccgtc    540 ggttgtgttc cactccaaag aacagttttt ggaggttttt ttacaagagg atgtaatcaa    600
cctctaaaca acatggcaaa acaatttaac gcaagacttt ctccagcttt agattcttta    660
gataaagagc tagatggtgt tatcctttac attaatgttt atgatactct tttcgacatg    720
atccaacacc ctaaaaaata cggttttgag gtagctgata gaggatgttg cggtaaagga    780
ttgcttgcga tatcctattt gtgtaactca ttgaacccat ttacgtgttc taattcttca    840
gcatacatat tttgggatag ctatcatcca tctgaaagag cttatcaagt tatcgtcgac    900
aatttactcg acaaatattt gagcaaagtc tattga                             936
```

<210> SEQ ID NO 2
<211> LENGTH: 311
<212> TYPE: PRT
<213> ORGANISM: Arabidopsis thaliana

<400> SEQUENCE: 2

```
Met Asp Thr Gly Asn Asn Asn Leu Pro Thr Leu Leu Lys Cys Asn
1               5                   10                  15

Phe Pro Pro Tyr Gly Lys Asp Tyr Pro Gly Gly Phe Ala Thr Gly Arg
                20                  25                  30

Phe Ser Asp Gly Arg Val Pro Ser Asp Leu Ile Ala Glu Lys Leu Gly
            35                  40                  45

Leu Ala Lys Thr Leu Pro Ala Tyr Met Asn Pro Tyr Leu Lys Pro Glu
        50                  55                  60

Asp Leu Leu Lys Gly Val Thr Phe Ala Ser Gly Thr Gly Tyr Asp
65                  70                  75                  80

Pro Leu Thr Ala Lys Ile Met Ser Val Ile Ser Val Trp Asp Gln Leu
                85                  90                  95

Ile Asn Phe Lys Glu Tyr Ile Ser Lys Ile Lys Arg His Phe Gly Glu
            100                 105                 110

Glu Lys Ala Lys Asp Ile Leu Glu His Ser Phe Phe Leu Val Val Ser
        115                 120                 125

Ser Ser Asn Asp Leu Ala His Thr Tyr Leu Ala Gln Thr His Arg Tyr
    130                 135                 140

Asp Arg Thr Ser Tyr Ala Asn Phe Leu Ala Asp Ser Ala Val His Phe
145                 150                 155                 160

Val Arg Glu Leu His Lys Leu Gly Ala Arg Lys Ile Gly Val Phe Ser
                165                 170                 175

Ala Val Pro Val Gly Cys Val Pro Leu Gln Arg Thr Val Phe Gly Gly
            180                 185                 190

Phe Phe Thr Arg Gly Cys Asn Gln Pro Leu Asn Asn Met Ala Lys Gln
        195                 200                 205

Phe Asn Ala Arg Leu Ser Pro Ala Leu Asp Ser Leu Asp Lys Glu Leu
    210                 215                 220

Asp Gly Val Ile Leu Tyr Ile Asn Val Tyr Asp Thr Leu Phe Asp Met
225                 230                 235                 240

Ile Gln His Pro Lys Lys Tyr Gly Phe Glu Val Ala Asp Arg Gly Cys
                245                 250                 255

Cys Gly Lys Gly Leu Leu Ala Ile Ser Tyr Leu Cys Asn Ser Leu Asn
            260                 265                 270

Pro Phe Thr Cys Ser Asn Ser Ser Ala Tyr Ile Phe Trp Asp Ser Tyr
        275                 280                 285

His Pro Ser Glu Arg Ala Tyr Gln Val Ile Val Asp Asn Leu Leu Asp
```

```
            290                 295                 300
Lys Tyr Leu Ser Lys Val Tyr
305                 310

<210> SEQ ID NO 3
<211> LENGTH: 1050
<212> TYPE: DNA
<213> ORGANISM: Arabidopsis thaliana

<400> SEQUENCE: 3
atgaagattc aaatattatt gttcgctttg gttttaatct tcgtggaagc taatgcagcg      60
acgcaaggaa aaacacaac  aatcccagca ctaatagttt ttggagattc aataatggat     120
acaggaaata acaataatct tcccactctt ctaaagtgta actttcctcc atatggaaaa     180
gattatcctg gaggcttcgc tactggaaga ttttctgatg gaagagttcc ttctgatctt     240
attgcggaaa agttgggatt ggctaagaca ttaccagcat atatgaatcc gtatttgaag     300
ccagaggatc ttcttaaagg tgtaacattt gcatctggag aactggttta tgatccattg     360
acagcaaaaa ttatgtcagt aatatcggtg tgggatcaac tcataaattt caaagaatat     420
atatcaaaga tcaagaggca tttcggagaa gaaaaagcca agatatcttt ggaacatagt     480
ttctttcttg tggtgtctag tagcaatgac cttgctcaca cttatttagc tcaaactcat     540
cgatatgatc gtacctctta tgccaatttc ttggctgact ctgctgtcca tttcgtgaga     600
gaattacata agcttggagc tcggaaaata ggagtgttta gtgcagtccc cgtcggttgt     660
gttccactcc aagaacagt  ttttggaggt tttttacaa  gaggatgtaa tcaacctcta     720
aacaacatgg caaaacaatt taacgcaaga cttttctccag ctttagattc tttagataaa     780
gagctagatg gtgttatcct ttacattaat gtttatgata ctcttttcga catgatccaa     840
caccctaaaa aatacggttt tgaggtagct gatagaggat gttgcggtaa aggattgctt     900
gcgatatcct atttgtgtaa ctcattgaac ccatttacgt gttctaattc ttcagcatac     960
atattttggg atagctatca tccatctgaa agagcttatc aagttatcgt cgacaattta    1020
ctcgacaaat atttgagcaa agtctattga                                     1050

<210> SEQ ID NO 4
<211> LENGTH: 349
<212> TYPE: PRT
<213> ORGANISM: Arabidopsis thaliana

<400> SEQUENCE: 4

Met Lys Ile Gln Ile Leu Leu Phe Ala Leu Val Leu Ile Phe Val Glu
1               5                   10                  15

Ala Asn Ala Ala Thr Gln Gly Lys Asn Thr Thr Ile Pro Ala Leu Ile
            20                  25                  30

Val Phe Gly Asp Ser Ile Met Asp Thr Gly Asn Asn Asn Asn Leu Pro
        35                  40                  45

Thr Leu Leu Lys Cys Asn Phe Pro Pro Tyr Gly Lys Asp Tyr Pro Gly
    50                  55                  60

Gly Phe Ala Thr Gly Arg Phe Ser Asp Gly Arg Val Pro Ser Asp Leu
65                  70                  75                  80

Ile Ala Glu Lys Leu Gly Leu Ala Lys Thr Leu Pro Ala Tyr Met Asn
                85                  90                  95

Pro Tyr Leu Lys Pro Glu Asp Leu Leu Lys Gly Val Thr Phe Ala Ser
            100                 105                 110

Gly Gly Thr Gly Tyr Asp Pro Leu Thr Ala Lys Ile Met Ser Val Ile
```

```
                115                 120                 125
Ser Val Trp Asp Gln Leu Ile Asn Phe Lys Glu Tyr Ile Ser Lys Ile
    130                 135                 140

Lys Arg His Phe Gly Glu Glu Lys Ala Lys Asp Ile Leu Glu His Ser
145                 150                 155                 160

Phe Phe Leu Val Val Ser Ser Asn Asp Leu Ala His Thr Tyr Leu
                165                 170                 175

Ala Gln Thr His Arg Tyr Asp Arg Thr Ser Tyr Ala Asn Phe Leu Ala
            180                 185                 190

Asp Ser Ala Val His Phe Val Arg Glu Leu His Lys Leu Gly Ala Arg
        195                 200                 205

Lys Ile Gly Val Phe Ser Ala Val Pro Val Gly Cys Val Pro Leu Gln
    210                 215                 220

Arg Thr Val Phe Gly Gly Phe Phe Thr Arg Gly Cys Asn Gln Pro Leu
225                 230                 235                 240

Asn Asn Met Ala Lys Gln Phe Asn Ala Arg Leu Ser Pro Ala Leu Asp
                245                 250                 255

Ser Leu Asp Lys Glu Leu Asp Gly Val Ile Leu Tyr Ile Asn Val Tyr
            260                 265                 270

Asp Thr Leu Phe Asp Met Ile Gln His Pro Lys Lys Tyr Gly Phe Glu
        275                 280                 285

Val Ala Asp Arg Gly Cys Cys Gly Lys Gly Leu Leu Ala Ile Ser Tyr
    290                 295                 300

Leu Cys Asn Ser Leu Asn Pro Phe Thr Cys Ser Asn Ser Ser Ala Tyr
305                 310                 315                 320

Ile Phe Trp Asp Ser Tyr His Pro Ser Glu Arg Ala Tyr Gln Val Ile
                325                 330                 335

Val Asp Asn Leu Leu Asp Lys Tyr Leu Ser Lys Val Tyr
            340                 345

<210> SEQ ID NO 5
<211> LENGTH: 1981
<212> TYPE: DNA
<213> ORGANISM: Arabidopsis thaliana

<400> SEQUENCE: 5
agcgtgaatg acgataataa ccattatttc tggtatgtat atatatagcc ttctgtccca    60
agatgctcat cactcacaat atggacaaaa cacaaacttg gtcttgaaga aaccaatacc   120
aaaaccccaa accgcagcgt ttaatcaaga atcgactatg gcttctacta ccttacttcc   180
ttctacttca acccaattcc tcgaccgaac tttctcaact tcatcttcct cttcgagacc   240
taaacttcaa tctctatctt tttcctcaac acttagaaaa aagaaactag tagtcccctg   300
ctatgtttct tcctccgtca acaaaaaatc ttccgtctcg tcttctctcc aatctccgac   360
attcaaacca ccgtcttgga agaaactatg taacgatgtc accaacttga tccccaaaac   420
gacgaatcag aatccaaaat taaacccggt gcagagaacc gccgctatgg ttttagacgc   480
ggtggaaaac gccatgatct cacacgagcg ccgccgtcat ccccatccta aaacggcgga   540
tcctgccgtc caaatagccg ggaacttctt cccggtaccg gagaaacctg tcgtgcataa   600
ccttccggtg actggaacag taccagaatg cattcaagga gtttacgtca gaaacggagc   660
aaatccactt cacaaaccag tctccggcca ccatttgttc gacggagacg gtatggtaca   720
cgctgtccgg ttcgataacg gctcggttag ctacgcttgt cggtttaccg aaacaaaccg   780
gttggttcaa gaacgtgaat gtggtcgtcc ggttttcccc aaagcaattg gagagcttca   840
```

-continued

```
cggacattta ggaatcgcca agcttatgct cttcaatacc cgcgggctat ttgggttagt    900
cgacccgacc ggaggactcg gtgtcgctaa cgccggttta gtttatttca atggtcatct    960
cttagccatg tccgaagacg atttaccgta ccatgtcaaa gttactcaaa ccggagattt   1020
agaaacttcg ggtcggtacg atttcgacgg tcagttaaaa tcaacaatga tagcccaccc   1080
gaaaatcgat cccgaaaccc gagaactctt cgctttaagc tacgacgtcg tttcaaagcc   1140
ttacttaaaa tacttcagat tcacatccga cggtgagaaa tcaccagacg tcgagattcc   1200
gcttgatcaa ccaacgatga tccacgattt cgcgatcact gagaatttcg tagtgattcc   1260
agaccaacaa gtggtattcc gattgccgga gatgataaga ggtggttctc cggtggttta   1320
cgacgagaag aagaaatcaa gattcgggat tttgaataaa aacgcgaaag atgcttcgtc   1380
gattcaatgg atcgaagtac agattgtttt tgtttccat ctatggaact cttgggaaga    1440
accagaaaca gacgaggttg tcgtgattgg atcatgcatg acgccacctg attcaatttt   1500
caacgaacac gacgaaacac ttcagagtgt tttgtcggag ataaggctaa accttaaaac   1560
aggggaatca acacgtagac cggttatctc ggaacaagtt aatctcgaag ctggtatggt   1620
caaccggaat ttattaggta gaaaaacccg gtatgcttat ctggctttaa ccgaaccgtg   1680
gcctaaagtg tccggtttcg ctaaagtgga cttatcgacc ggagagattc gaaagtatat   1740
ttacggagag gggaaatacg gaggagagcc tctgtttcta ccttccggtg acggagaaga   1800
agacggaggt tacataatgg tgttcgttca cgacgaggag aaggtgaaat cggaactcca   1860
actcataaac gccgttaata tgaagcttga agctaccgta acgcttccgt cgagagtgcc   1920
ttacggtttc cacggaacgt tcatcagtaa ggaagattta tcgaagcaag ctttgtgtta   1980
g                                                                   1981
```

<210> SEQ ID NO 6
<211> LENGTH: 657
<212> TYPE: PRT
<213> ORGANISM: Arabidopsis thaliana

<400> SEQUENCE: 6

```
Met Thr Ile Ile Thr Ile Ile Ser Gly Met Tyr Ile Tyr Ser Leu Leu
1               5                   10                  15

Ser Gln Asp Ala His His Ser Gln Tyr Gly Gln Asn Thr Asn Leu Val
            20                  25                  30

Leu Lys Lys Pro Ile Pro Lys Pro Gln Thr Ala Ala Phe Asn Gln Glu
        35                  40                  45

Ser Thr Met Ala Ser Thr Thr Leu Leu Pro Ser Thr Ser Thr Gln Phe
    50                  55                  60

Leu Asp Arg Thr Phe Ser Thr Ser Ser Ser Ser Arg Pro Lys Leu
65                  70                  75                  80

Gln Ser Leu Ser Phe Ser Ser Thr Leu Arg Asn Lys Lys Leu Val Val
                85                  90                  95

Pro Cys Tyr Val Ser Ser Val Asn Lys Lys Ser Ser Val Ser Ser
            100                 105                 110

Ser Leu Gln Ser Pro Thr Phe Lys Pro Pro Ser Trp Lys Lys Leu Cys
        115                 120                 125

Asn Asp Val Thr Asn Leu Ile Pro Lys Thr Thr Asn Gln Asn Pro Lys
    130                 135                 140

Leu Asn Pro Val Gln Arg Thr Ala Ala Met Val Leu Asp Ala Val Glu
145                 150                 155                 160
```

```
Asn Ala Met Ile Ser His Glu Arg Arg His Pro His Pro Lys Thr
            165                 170                 175

Ala Asp Pro Ala Val Gln Ile Ala Gly Asn Phe Phe Pro Val Pro Glu
            180                 185                 190

Lys Pro Val Val His Asn Leu Pro Val Thr Gly Thr Val Pro Glu Cys
            195                 200                 205

Ile Gln Gly Val Tyr Val Arg Asn Gly Ala Asn Pro Leu His Lys Pro
    210                 215                 220

Val Ser Gly His His Leu Phe Asp Gly Asp Gly Met Val His Ala Val
225                 230                 235                 240

Arg Phe Asp Asn Gly Ser Val Ser Tyr Ala Cys Arg Phe Thr Glu Thr
                245                 250                 255

Asn Arg Leu Val Gln Glu Arg Glu Cys Gly Arg Pro Val Phe Pro Lys
            260                 265                 270

Ala Ile Gly Glu Leu His Gly His Leu Gly Ile Ala Lys Leu Met Leu
    275                 280                 285

Phe Asn Thr Arg Gly Leu Phe Gly Leu Val Asp Pro Thr Gly Gly Leu
    290                 295                 300

Gly Val Ala Asn Ala Gly Leu Val Tyr Phe Asn Gly His Leu Leu Ala
305                 310                 315                 320

Met Ser Glu Asp Asp Leu Pro Tyr His Val Lys Val Thr Gln Thr Gly
                325                 330                 335

Asp Leu Glu Thr Ser Gly Arg Tyr Asp Phe Asp Gly Gln Leu Lys Ser
            340                 345                 350

Thr Met Ile Ala His Pro Lys Ile Asp Pro Glu Thr Arg Glu Leu Phe
    355                 360                 365

Ala Leu Ser Tyr Asp Val Val Ser Lys Pro Tyr Leu Lys Tyr Phe Arg
    370                 375                 380

Phe Thr Ser Asp Gly Glu Lys Ser Pro Asp Val Glu Ile Pro Leu Asp
385                 390                 395                 400

Gln Pro Thr Met Ile His Asp Phe Ala Ile Thr Glu Asn Phe Val Val
                405                 410                 415

Ile Pro Asp Gln Gln Val Val Phe Arg Leu Pro Glu Met Ile Arg Gly
            420                 425                 430

Gly Ser Pro Val Val Tyr Asp Glu Lys Lys Ser Arg Phe Gly Ile
    435                 440                 445

Leu Asn Lys Asn Ala Lys Asp Ala Ser Ser Ile Gln Trp Ile Glu Val
    450                 455                 460

Pro Asp Cys Phe Cys Phe His Leu Trp Asn Ser Trp Glu Glu Pro Glu
465                 470                 475                 480

Thr Asp Glu Val Val Val Ile Gly Ser Cys Met Thr Pro Pro Asp Ser
                485                 490                 495

Ile Phe Asn Glu His Asp Glu Thr Leu Gln Ser Val Leu Ser Glu Ile
            500                 505                 510

Arg Leu Asn Leu Lys Thr Gly Glu Ser Thr Arg Arg Pro Val Ile Ser
    515                 520                 525

Glu Gln Val Asn Leu Glu Ala Gly Met Val Asn Arg Asn Leu Leu Gly
    530                 535                 540

Arg Lys Thr Arg Tyr Ala Tyr Leu Ala Leu Thr Glu Pro Trp Pro Lys
545                 550                 555                 560

Val Ser Gly Phe Ala Lys Val Asp Leu Ser Thr Gly Glu Ile Arg Lys
                565                 570                 575

Tyr Ile Tyr Gly Glu Gly Lys Tyr Gly Gly Glu Pro Leu Phe Leu Pro
```

-continued

```
              580                 585                 590
Ser Gly Asp Gly Glu Glu Asp Gly Gly Tyr Ile Met Val Phe Val His
        595                 600                 605

Asp Glu Glu Lys Val Lys Ser Glu Leu Gln Leu Ile Asn Ala Val Asn
    610                 615                 620

Met Lys Leu Glu Ala Thr Val Thr Leu Pro Ser Arg Val Pro Tyr Gly
625                 630                 635                 640

Phe His Gly Thr Phe Ile Ser Lys Glu Asp Leu Ser Lys Gln Ala Leu
                645                 650                 655

Cys

<210> SEQ ID NO 7
<211> LENGTH: 2058
<212> TYPE: DNA
<213> ORGANISM: Arabidopsis thaliana

<400> SEQUENCE: 7
atggagatca gaagatcaac agaagaagtt gaagagaatc atgtaatgca gattacagga      60
agcaatggca tagttcacaa catggagttc atgccacaag cttacctcag aaaccaatac     120
tcatccgaga ttgacattga tgaagagttc gtttccactt atcctctcga agatgcccct     180
cttcccatct ttctcaagtt tgaagatgtg agtataagg tgagaaacag tcatgctagc      240
tcagcaaacc tggtgaaaac aatggtgtca aggtggtaa cacatacaaa tccggatcca      300
gatggataca agcacatttt gaaaggcata acaggaagca caggtcctgg cgaaatcctt     360
gcgctaatgg ggccttcggg tagtggcaaa acaactcttc tgaagataat gggaggaaga     420
ttgacagata atgtcaaggg gaagcttacc tataatgaca ttccttacag tccatctgtt     480
aagaggagaa ttggctttgt gacgcaagac gatgttctgt tgccacaact tactgtggaa     540
gagaccttgg catttgctgc gttttttaaga cttccaagta gcatgagcaa ggaacaaaaa     600
tacgccaaaa tagagatgat catcaaagag ctcggcctcg aaagatgccg tcggacaaga     660
gttggaggag ttttgtcaa gggaatatca ggtggagaaa gaaaaagagc aagtatagct      720
tatgagattc tcgtagatcc ttctctgttg cttctagacg agccaacttc tggacttgac     780
tccacttctg ccaccaaact tcttcatatt cttcaaggag tagctaaggc aggcaggacc     840
gttataacga caattcacca accatcaagc agaatgtttc acatgtttga caagctctta     900
ctgatatcag aaggacaccc tgccttttac ggcaaagcca gagaatctat ggagtatttc     960
tcatctttga gaatcttacc tgagattgca atgaacccag cagagttctt gctagacttg    1020
gcaaccggac aagtttcaga cattagtcta cccgacgaac tattggctgc caaaactgca    1080
cagcctgatt ctgaggaagt tttactcaaa tacttgaaac aaaggtacaa gacagacttg    1140
gagccaaaag agaaggaaga aaatcataga aatagaaagg ccccagagca tcttcaaata    1200
gcaatccaag tgaagaagga ctggactctt tcatggtggg atcagttctt gattctttca    1260
agaagaacat tcagagagcg gcgtagagat tactttgata agctaaggct agttcaatca    1320
cttggtgtgg ccgtcgtgtt gggtcttctc tggtggaagt caaagacaga tacagaggct    1380 cacctttagag accaagttgg tttgatgttc tatatctgca tcttctggac atcgtcatca    1440
ctctttggag cagtatacgt gttccccttc gagaagatct acctggtgaa agaaagaaaa    1500
gcagaaatgt acagacttag tgtgtattac gtatgcagta cactatgtga tatggtggca    1560
cacgttttgt acccgacatt cttcatgatc attgtctact tcatggctga gttcaatagg    1620
aacatcccct gcttcctttt caccgtgttg acaatactac tgatagccat cactagccaa    1680
```

-continued

```
ggtgcaggag agttcttagg agcttcagta ttgagcatta agagagctgg tatgatcgcc      1740
tctttggtac taatgctgtt tctactaacc ggaggttact atgtccagca cataccaaaa      1800
ttcatgcagt ggttgaagta cttgtcattc atgcactacg gcttcaggct acttttgaaa      1860
gttcaatact cagctgacca acttttcgaa tgtgggagca aaggcggctg caggacactg      1920
caaagctcat cgtcctttga cacgataaac ttgaatggcg gcttacaaga actgtgggtt      1980
ctgcttgcca tggcattcgg ctaccgtctc tgtgcatact tttgccttcg caagaaaata      2040
agcatttgcc atctttga                                                    2058
```

<210> SEQ ID NO 8
<211> LENGTH: 685
<212> TYPE: PRT
<213> ORGANISM: Arabidopsis thaliana

<400> SEQUENCE: 8

```
Met Glu Ile Arg Arg Ser Thr Glu Glu Val Glu Asn His Val Met
 1               5                  10                  15

Gln Ile Thr Gly Ser Asn Gly Ile Val His Asn Met Glu Phe Met Pro
            20                  25                  30

Gln Ala Tyr Leu Arg Asn Gln Tyr Ser Ser Glu Ile Asp Ile Asp Glu
        35                  40                  45

Glu Phe Val Ser Thr Tyr Pro Leu Glu Asp Ala Pro Leu Pro Ile Phe
    50                  55                  60

Leu Lys Phe Glu Asp Val Glu Tyr Lys Val Arg Asn Ser His Ala Ser
65                  70                  75                  80

Ser Ala Asn Leu Val Lys Thr Met Val Ser Lys Val Val Thr His Thr
                85                  90                  95

Asn Pro Asp Pro Asp Gly Tyr Lys His Ile Leu Lys Gly Ile Thr Gly
            100                 105                 110

Ser Thr Gly Pro Gly Glu Ile Leu Ala Leu Met Gly Pro Ser Gly Ser
        115                 120                 125

Gly Lys Thr Thr Leu Leu Lys Ile Met Gly Gly Arg Leu Thr Asp Asn
    130                 135                 140

Val Lys Gly Lys Leu Thr Tyr Asn Asp Ile Pro Tyr Ser Pro Ser Val
145                 150                 155                 160

Lys Arg Arg Ile Gly Phe Val Thr Gln Asp Asp Val Leu Leu Pro Gln
                165                 170                 175

Leu Thr Val Glu Glu Thr Leu Ala Phe Ala Ala Phe Leu Arg Leu Pro
            180                 185                 190

Ser Ser Met Ser Lys Glu Gln Lys Tyr Ala Lys Ile Glu Met Ile Ile
        195                 200                 205

Lys Glu Leu Gly Leu Glu Arg Cys Arg Arg Thr Arg Val Gly Gly Gly
    210                 215                 220

Phe Val Lys Gly Ile Ser Gly Gly Glu Arg Lys Arg Ala Ser Ile Ala
225                 230                 235                 240

Tyr Glu Ile Leu Val Asp Pro Ser Leu Leu Leu Asp Glu Pro Thr
                245                 250                 255

Ser Gly Leu Asp Ser Thr Ser Ala Thr Lys Leu Leu His Ile Leu Gln
            260                 265                 270

Gly Val Ala Lys Ala Gly Arg Thr Val Ile Thr Thr Ile His Gln Pro
        275                 280                 285

Ser Ser Arg Met Phe His Met Phe Asp Lys Leu Leu Leu Ile Ser Glu
    290                 295                 300
```

-continued

```
Gly His Pro Ala Phe Tyr Gly Lys Ala Arg Glu Ser Met Glu Tyr Phe
305                 310                 315                 320

Ser Ser Leu Arg Ile Leu Pro Glu Ile Ala Met Asn Pro Ala Glu Phe
            325                 330                 335

Leu Leu Asp Leu Ala Thr Gly Gln Val Ser Asp Ile Ser Leu Pro Asp
        340                 345                 350

Glu Leu Leu Ala Ala Lys Thr Ala Gln Pro Asp Ser Glu Glu Val Leu
    355                 360                 365

Leu Lys Tyr Leu Lys Gln Arg Tyr Lys Thr Asp Leu Glu Pro Lys Glu
370                 375                 380

Lys Glu Glu Asn His Arg Asn Arg Lys Ala Pro Glu His Leu Gln Ile
385                 390                 395                 400

Ala Ile Gln Val Lys Lys Asp Trp Thr Leu Ser Trp Asp Gln Phe
            405                 410                 415

Leu Ile Leu Ser Arg Arg Thr Phe Arg Glu Arg Arg Asp Tyr Phe
        420                 425                 430

Asp Lys Leu Arg Leu Val Gln Ser Leu Gly Val Ala Val Val Leu Gly
    435                 440                 445

Leu Leu Trp Trp Lys Ser Lys Thr Asp Thr Glu Ala His Leu Arg Asp
450                 455                 460

Gln Val Gly Leu Met Phe Tyr Ile Cys Ile Phe Trp Thr Ser Ser Ser
465                 470                 475                 480

Leu Phe Gly Ala Val Tyr Val Phe Pro Phe Glu Lys Ile Tyr Leu Val
            485                 490                 495

Lys Glu Arg Lys Ala Glu Met Tyr Arg Leu Ser Val Tyr Tyr Val Cys
        500                 505                 510

Ser Thr Leu Cys Asp Met Val Ala His Val Leu Tyr Pro Thr Phe Phe
    515                 520                 525

Met Ile Ile Val Tyr Phe Met Ala Glu Phe Asn Arg Asn Ile Pro Cys
530                 535                 540

Phe Leu Phe Thr Val Leu Thr Ile Leu Leu Ile Ala Ile Thr Ser Gln
545                 550                 555                 560

Gly Ala Gly Glu Phe Leu Gly Ala Ser Val Leu Ser Ile Lys Arg Ala
            565                 570                 575

Gly Met Ile Ala Ser Leu Val Leu Met Leu Phe Leu Leu Thr Gly Gly
        580                 585                 590

Tyr Tyr Val Gln His Ile Pro Lys Phe Met Gln Trp Leu Lys Tyr Leu
    595                 600                 605

Ser Phe Met His Tyr Gly Phe Arg Leu Leu Leu Lys Val Gln Tyr Ser
610                 615                 620

Ala Asp Gln Leu Phe Glu Cys Gly Ser Lys Gly Gly Cys Arg Thr Leu
625                 630                 635                 640

Gln Ser Ser Ser Ser Phe Asp Thr Ile Asn Leu Asn Gly Gly Leu Gln
            645                 650                 655

Glu Leu Trp Val Leu Leu Ala Met Ala Phe Gly Tyr Arg Leu Cys Ala
        660                 665                 670

Tyr Phe Cys Leu Arg Lys Lys Ile Ser Ile Cys His Leu
    675                 680                 685
```

GENERATION OF PLANTS WITH ALTERED OIL, PROTEIN, OR FIBER CONTENT

CROSS REFERENCE TO RELATED APPLICATION(S)

This application claims the benefit of U.S. Provisional Application No. 60/870,357, filed Dec. 15, 2006, the entirety of which is incorporated herein by reference.

FIELD OF THE DISCLOSURE

The present disclosure is related to modified plants with altered oil, protein, and/or fiber content, as well as methods of making modified plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has not been able to achieve seed oil content above 9%. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al, 1995 Bio/Technology 13:577-582) increases the availability of this essential amino acid and decreases the need for nutritional supplements. Soybean varieties with increased seed protein were shown to contain considerably more metabolizable energy than conventional varieties (Edwards et al., 1999, Poultry Sci. 79:525-527). Decreasing the phytate content of corn seed has been shown to increase the bioavailability of amino acids in animal feeds (Douglas et al., 2000, Poultry Sci. 79:1586-1591) and decreasing oligosaccharide content in soybean meal increases the metabolizable energy in the meal (Parsons et al., 2000, Poultry Sci. 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952, 544; PCT Application No. WO9411516) demonstrates that Arabidopsis is an excellent model for oil metabolism in these crops. Biochemical screens of seed oil composition have identified Arabidopsis genes for many critical biosynthetic enzymes and have led to identification of agronomically important gene orthologs. For instance, screens using chemically mutagenized populations have identified lipid mutants whose seeds display altered fatty acid composition (Lemieux et al., 1990, Theor. Appl Genet. 80: 234-240; James and Dooner, 1990, Theor. Appl Genet. 80: 241-245). T-DNA mutagenesis screens (Feldmann et al., 1989, Science 243: 1351-1354) that detected altered fatty acid composition identified the omega 3 desaturase (FAD3) and delta-12 desaturase (FAD2) genes (U.S. Pat. No. 5,952,544; Yadav et al., 1993, Plant Physiol. 103: 467-476; Okuley et al., 1994, Plant Cell 6(1):147-158). A screen which focused on oil content rather than oil quality, analyzed chemically-induced mutants for wrinkled seeds or altered seed density, from which altered seed oil content was inferred (Focks and Benning, 1998, Plant Physiol. 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122: 1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, *9th International Conference on Arabidopsis Research*, Univ. of Wisconsin-Madison, June 24-28, Abstract 165).

SUMMARY

Provided herein are modified plants having an altered phenotype. Modified plants with an altered phenotype may include an improved oil quantity and/or an improved meal quality phenotype. The altered phenotype in a modified plant may also include altered oil, protein, and/or fiber content in any part of the modified plant, for example in the seeds. In some embodiments of a modified plant, the altered phenotype is an increase in the oil content of the seed (a high oil phenotype). In other embodiments, the altered phenotype may be an increase in protein content in the seed and/or a decrease in the fiber content of the seed. Also provided is seed meal derived from the seeds of modified plants, wherein the seeds have altered protein content and/or altered fiber content. Further provided is oil derived from the seeds of modified plants, wherein the seeds have altered oil content. Any of these changes can lead to an increase in the AME from the seed or seed meal from modified plants, relative to control or wild-type plants. Also provided herein is meal, feed, or food produced from any part of the modified plant with an altered phenotype.

In certain embodiments, the disclosed modified plants include transgenic plants having a transformation vector comprising a HIO nucleotide sequence (or HIO gene alias) that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Examples of the disclosed transgenic plant are produced by a method that comprises introducing into progenitor cells of the plant a plant transformation vector comprising a HIO nucleotide sequence that encodes, or is complementary to a sequence that encodes, a HIO polypeptide, and growing the transformed progenitor cells to produce a transgenic plant, wherein the HIO polynucleotide sequence is expressed, causing an altered phenotype in the transgenic plant. In some specific, non-limiting examples, the method produces transgenic plants wherein expression of the HIO polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen, radiation, or ultraviolet light. In some embodiments of the method, the plant is bred to generate progeny which inherit the allele and express the altered phenotype. In particular embodiments of the method, the method employs candidate gene/QTL methodology or TILLING methodology.

Also provided herein is a modified plant cell having an altered phenotype. In some embodiments, the modified plant cell includes a transformation vector comprising a HIO nucleotide sequence that encodes or is complementary to a sequence that encodes a HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel FM et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "altered phenotype" refers to plants, or any part of a plant (for example, seeds, or meal produced from seeds), with an altered oil, protein, and/or fiber content (phenotype). As provided herein, altered oil, protein (for example, digestible protein) and/or fiber content includes either an increased or decreased level of oil, protein (for example, digestible protein) and/or fiber content in plants, seeds or seed meal. Any combination of these changes can lead to an altered phenotype. For example, in one specific non-limiting example, an altered phenotype can refer to increased oil and decreased fiber content. In another specific non-limiting example, an altered phenotype can refer to unchanged protein and decreased fiber content. In another specific non-limiting example, an altered phenotype can refer to increased oil and protein and decreased fiber. In yet other non-limiting examples, an altered phenotype can refer to increased oil and protein and unchanged fiber content; unchanged oil, increased protein, and decreased fiber content; or increased oil, increased protein, and decreased fiber content. It is also provided that any combination of these changes can lead to an increase in the AME (available metabolizable energy) from the seed or meal generated from the seed. An altered phenotype also includes an improved seed quality (ISQ) phenotype or an improved seed meal quality phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a modified plant with an increase in AME includes modified plants with altered seed oil, digestible protein, total protein and/or fiber content, resulting in an increase in the value of animal feed derived from the seed.

As used herein, the term "content" refers to the type and relative amount of, for instance, a seed or seed meal component.

As used herein, the term "seed oil" refers to the total amount of oil within the seed.

As used herein, the term "seed fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "seed total protein" refers to the total amount of protein within the seed.

As used herein, the term "seed digestible protein" refers to the seed protein that is able to be digested by enzymes in the digestive track of an animal. It is a subset of the total protein content.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include a HIO nucleic acid sequence, or a fragment, derivative (variant), or ortholog or paralog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

The term "homolog" refers to any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure (mutations). The term "paralog" refers to homologs in the same species that evolved by genetic duplication of a common ancestral gene. In many cases, paralogs exhibit related (but not always identical functions). As used herein, the term homolog encompasses both orthologs and paralogs. To the extent that a particular species has evolved multiple related genes from an ancestral DNA sequence shared with another species, the term ortholog can encompass the term paralog.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-modified or wild-type plant. "Under-expression" refers to decreased expression of a polynucleotide and/or polypeptide sequence, enerally of an endogenous gene, relative to its expression in a wild-type plant. The terms "mis-expression"

and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type or native plant is also a control plant. In another embodiment, a wild-type or native plant is a non-transgenic or non-mutated plant. In yet another embodiment, a wild-type or native plant is a non-modified plant.

As used herein, the term "modified" regarding a plant, refers to a plant with an altered phenotype (for example, a plant generated by genetic engineering, mutagenesis, or breeding methods). A genetically engineered plant can also be a transgenic plant. In particular embodiments, modified plants generated by breeding methods are first mutagenized using any one of a variety of mutagens, such as a chemical mutagen, radiation, or ultraviolet light. Modified plants can have any combination of an altered oil content, an altered protein content, and/or an altered fiber content in any part of the transgenic plant, for example the seeds, relative to a similar non-modified plant.

As used herein, the term "altered" refers to a change (either an increase or a decrease) of a plant trait or phenotype (for example, oil content, protein content, and/or fiber content) in a modified plant, relative to a similar non-modified plant. In one specific, non-limiting example, a modified plant with an altered trait includes a plant with an increased oil content, increased protein content, and/or decreased fiber content relative to a similar non-modified plant. In another specific, non-limiting example, a modified plant with an altered trait includes unchanged oil content, increased protein content, and/or decreased fiber content relative to a similar non-modified plant. In yet another specific, non-limiting example, a modified plant with an altered trait includes an increased oil content, increased protein content, and/or unchanged fiber content relative to a similar non-modified plant.

An "interesting phenotype (trait)" with reference to a modified plant refers to an observable or measurable phenotype demonstrated by a TI and/or subsequent generation plant, which is not displayed by the corresponding non-modified plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such modified plants may have an improved phenotype, such as an altered oil, protein, and/or fiber phenotype. Meal generated from seeds of a modified plant with an improved phenotype can have improved (increased) meal quality. In a specific, non-limiting example of meal with an improved (increased) quality phenotype, meal is generated from a seed of a modified plant, wherein the seed has increased protein content and/or decreased fiber content, relative to a similar non-modified plant.

The phrase "altered oil content phenotype" refers to a measurable phenotype of a modified plant, where the plant displays a statistically significant increase or decrease in overall oil content (i.e., the percentage of seed mass that is oil), as compared to the similar, but non-modified (for example, a non-transgenic or a non-mutated) plant. A high oil phenotype refers to an increase in overall oil content. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. Likewise, a decrease in oil content includes about a 1.0%, 1.5%, 2.0%, 2.5%, 3.0%, 3.5%, 4.0%, 4.5%, 5.0%, 7.5%, 10%, or more decrease in oil content, in various embodiments.

The phrase "altered protein content phenotype" refers to measurable phenotype of a modified plant, where the plant displays a statistically significant increase or decrease in overall protein content (i.e., the percentage of seed mass that is protein), as compared to the similar, but non-modified (for example, non-transgenic or non-mutated) plant. A high protein phenotype refers to an increase in overall protein content. An increase in protein content includes, in various embodiments, about a 1.0%, 1.5%, 2.0%, 2.5%, 3.0%, 3.5%, 4.0%, 4.5%, 5.0%, 7.5%, 10%, or more increase in total protein content. Likewise, an increase in digestible protein content includes, in various embodiments, about a 1.0%, 1.5%, 2.0%, 2.5%, 3.0%, 3.5%, 4.0%, 4.5%, 5.0%, 7.5%, 10%, or more increase in digestible protein content. A decrease in protein content includes about a 1.0%, 1.5%, 2.0%, 2.5%, 3.0%, 3.5%, 4.0%, 4.5%, 5.0%, 7.5%, 10%, or more decrease in total protein content, in various embodiments. Likewise, a decrease in digestible protein content includes, in various embodiments, about a 1.0%, 1.5%, 2.0%, 2.5%, 3.0%, 3.5%, 4.0%, 4.5%, 5.0%, 7.5%, 10%, or more decrease in digestible protein content. The phrase "altered fiber content phenotype" refers to measurable phenotype of a modified plant, where the plant displays a statistically significant increase or decrease in overall fiber content (i.e., the percentage of seed mass that is fiber), as compared to the similar, but non-modified (for example, non-transgenic or non-mutated) plant. A low fiber phenotype refers to decrease in overall fiber content. An increase in fiber content includes about a 1.0%, 1.5%, 2.0%, 2.5%, 3.0%, 3.5%, 4.0%, 4.5%, 5.0%, 7.5%, 10%, or more increase in fiber content. Likewise, a decrease in fiber content includes about a 1.0%, 1.5%, 2.0%, 2.5%, 3.0%, 3.5%, 4.0%, 4.5%, 5.0%, 7.5%, 10%, or more decrease in fiber content.

As used herein, a "mutant" or "mutated" polynucleotide sequence or gene differs from the corresponding wild-type polynucleotide sequence or gene either in terms of sequence or expression, where the difference contributes to an altered plant phenotype or trait. Relative to a plant or plant line, the term "mutant" or "mutated" refers to a plant or plant line which has an altered plant phenotype or trait, where the altered phenotype or trait is associated with the altered expression of a wild-type polynucleotide sequence or gene. The mutated polynucleotide sequence or gene can be generated by genetic engineering methods (such as activation tagging or transformation), by using one or more mutagens (for example, chemical mutagens, radiation, or ultraviolet light), or by using methods to alter a DNA sequence (for example, error prone PCR, DNA shuffling molecular breeding, site-directed mutagenesis, or introducing the gene into a mutagenizing organism such as *E. coli* or yeast strains that are deficient in DNA repair activity).

As used herein, the term "T1" refers to the generation of plants from the seed of T0 plants. The T1 generation is the first set of modified plants that can be selected by application of a selection agent, e.g., an antibiotic or herbicide, for which the modified plant contains the corresponding resistance gene. The term "T2" refers to the generation of plants by self-fertilization of the flowers of T1 plants, previously selected as being modified. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a modified plant cell having an altered phenotype. In particular embodiments, the modified plant cell is a transgenic plant cell. The transgenic plant cell includes a transformation vector comprising an HIO nucleotide sequence that encodes or is complementary to a sequence that encodes an HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are modified plants having an altered phenotype. Modified plants with an altered phenotype may include an improved (increased) oil quantity and/or an improved (increased) meal quality, as compared to the similar, but non-modified (for example, non-transgenic or non-mutated) plant. Modified plants with an altered phenotype may include altered oil, protein, and/or fiber content in any part of the modified plant, for example in the seeds, as compared to the similar, but non-modified (for example, non-transgenic or non-mutated) plant. In some embodiments of a modified plant, for example in plants with an improved or increased oil content phenotype, the altered phenotype includes an increase in the oil content of the seed (a high oil phenotype) from the plant, as compared to the similar, but non-modified (non-transgenic or non-mutated) plant. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. The altered phenotype can be an increase in one or more fatty acids, such as oleic acid, with a concomitant decrease in other fatty acids such as linoleic or linolinic acids. A change in fatty acid content includes about a 5%, 10%, 20%, 30%, 40%, 50%, 60%, 70%, 80%, 90%, 100% or more increase in a specific fatty acid. In other embodiments of a modified plant, for example in plants with an improved or increased meal quality phenotype, the altered phenotype may be an increase in protein content in the seed and/or a decrease in the fiber content of the seed. An increase in protein content includes about a 1.0%, 1.5%, 2.0%, 2.5%, 3.0%, 3.5%, 4.0%, 4.5%, 5.0%, 7.5%, 10%, or more increase in protein content, for instance total protein content or digestible protein content. This change in seed protein content can be the result of altered amounts of seed storage proteins such as albumins, globulins, prolamins, and glutelins. A decrease in fiber content includes about a 1.0%, 1.5%, 2.0%, 2.5%, 3.0%, 3.5%, 4.0%, 4.5%, 5.0%, 7.5%, 10%, or more decrease in fiber content. This change in fiber content can be the result of altered amounts of fibrous components such as cellulose, hemicellulose, lignin and pectins.

Also provided is seed meal derived from the seeds of modified plants, wherein the seeds have altered (for example, increased) protein (for example, digestible) content and/or altered (for example, decreased) fiber content. Further provided is oil derived from the seeds of modified plants, wherein the seeds have altered oil content. Any of these changes can lead to an increase in the AME from the seed or seed meal from modified plants, relative to control, non-transgenic, or wild-type plants. An increase in the AME includes about a 1.0%, 1.5%, 2.0%, 2.5%, 3.0%, 3.5%, 4.0%, 4.5%, 5.0%, 7.5%, 10%, or more increase in AME in the seed or seed meal, in various embodiments. Also provided herein is meal, feed, or food produced from any part of the modified plant with an altered phenotype.

In certain embodiments, the disclosed transgenic plants comprise a transformation vector comprising a HIO nucleotide sequence that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

Agrobacterium-mediated transformation is achieved through the use of a genetically engineered soil bacterium belonging to the genus Agrobacterium. A number of wild-type and disarmed strains of Agrobacterium tumefaciens and Agrobacterium rhizogenes harboring Ti or Ri plasmids can be used for gene transfer into plants. Gene transfer is done via the transfer of a specific DNA known as "T-DNA" that can be genetically engineered to carry any desired piece of DNA into many plant species.

Agrobacterium-mediated genetic transformation of plants involves several steps. The first step, in which the virulent Agrobacterium and plant cells are first brought into contact with each other, is generally called "inoculation." Following the inoculation, the Agrobacterium and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill or limit the growth of the Agrobacterium remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. Nos. 5,550,318; 5,538,880, 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin, neomycin, G418, bleomycin, methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, and 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Phenotype

An *Arabidopsis* activation tagging screen (ACTTAG) was used to identify the association between 1) ACTTAG plant lines with an altered oil, protein and/or fiber content (see columns 4, 5 and 6 respectively, of Table 1, below) and 2) the nucleic acid sequences identified in column 3 of Tables 2 and 3, wherein each nucleic acid sequence is provided with a gene alias or a HIO designation (HIO#; see column 1 in Tables 1, 2, and 3). The HIO designation is arbitrary and does not necessarily relate to a plant having a high oil (HIO) phenotype.

Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000, *Plant Physiology*, 122:1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

The association of a HIO nucleic acid sequence with an altered phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed HIO nucleic acid sequences and/or polypeptides may be employed in the development of transgenic plants having an altered, for example high oil, phenotype. HIO nucleic acid sequences may be used in the generation of transgenic plants, such as oilseed crops, that provide improved oil yield from oilseed processing and result in an increase in the quantity of oil recovered from seeds of the transgenic plant. HIO nucleic acid sequences may also be used in the generation of transgenic plants, such as feed grain crops, that provide an altered phenotype resulting in increased energy for animal feeding, for example, seeds or seed meal with an altered protein and/or fiber content, resulting in an increase in AME. HIO nucleic acid sequences may further be used to increase the oil content of specialty oil crops, in order to augment yield and/or recovery of desired unusual fatty acids. Specific non-limiting examples of unusual fatty acids are ricinoleic acid, vemolic acid and the very long chain polyunsaturated fatty acids docosahexaenoic acid (DHA) and eicosapentaenoic acid (EPA). Transgenic plants that have been genetically modified to express HIO polypeptides can be used in the production of seeds, wherein the transgenic plants are grown, and oil and seed meal are obtained from plant parts (e.g. seed) using standard methods.

HIO Nucleic Acids and Polypentides

The HIO designation for each of the HIO nucleic acid sequences discovered in the activation tagging screen described herein are listed in column 1 of Tables 1-3, below. The disclosed HIO polypeptides are listed in column 4 of Tables 2 and 3, below. The HIO designation is arbitrary and does not necessarily relate to a plant having a high oil (HIO) phenotype. As used herein, the gene alias or HIO designation refers to any polypeptide sequence (or the nucleic acid sequence that encodes it) that when expressed in a plant causes an altered phenotype in any part of the plant, for example the seeds. In one embodiment, a HIO polypeptide refers to a full-length HIO protein, or a fragment, derivative (variant), or ortholog or paralog thereof that is "functionally active," such that the protein fragment, derivative, or ortholog or paralog exhibits one or more or the functional activities associated with one or more of the disclosed full-length HIO polypeptides, for example, the amino acid sequences provided in the GenBank entry referenced in column 4 of Table 2, and 3 which correspond to the amino acid sequences set forth as SEQ ID NO: 2, SEQ ID NO: 4, SEQ ID NO: 6, or SEQ ID NO: 8, or an ortholog or paralog thereof. In one preferred embodiment, a functionally active HIO polypeptide causes an altered phenotype in a transgenic plant. In another embodiment, a functionally active HIO polypeptide causes an altered oil, protein, and/or fiber content phenotype (for example, an altered seed meal content phenotype) when mis-expressed in a plant. In other preferred embodiments, mis-expression of the HIO polypeptide causes a high oil (such as, increased oil), high protein (such as, increased total protein or digestible protein), and/or low fiber (such as, decreased fiber) phenotype in a plant. In yet other preferred embodiments, mis-expression of the HIO polypeptide causes unchanged oil, high protein (such as, increased total protein or digestible protein), and/or low fiber (such as, decreased fiber) phenotype in a plant. In another embodiment, mis-expression of the HIO polypeptide causes an improved AME of meal. In yet another embodiment, a functionally active HIO polypeptide can rescue defective (including deficient) endogenous HIO polypeptide activity when expressed in a plant or in plant cells; the rescuing polypeptide may be from the same or from a different species as the species with the defective polypeptide activity. The disclosure also provides feed, meal, grain, food, or seed comprising the HIO polypeptide, or a fragment, derivative (variant), or ortholog or paralog thereof.

In another embodiment, a functionally active fragment of a full length HIO polypeptide (for example, a functionally active fragment of a native polypeptide having the amino acid sequence set forth as SEQ ID NO: 2, SEQ ID NO: 4, SEQ ID NO: 6, or SEQ ID NO: 8, or a naturally occurring ortholog or paralog thereof) retains one or more of the biological properties associated with the full-length HIO polypeptide, such as signaling activity, binding activity, catalytic activity, or cellular or extra-cellular localizing activity. A HIO fragment preferably comprises a HIO domain, such as a C- or N-terminal or catalytic domain, among others, and preferably comprises at least 10, preferably at least 20, more preferably at least 25, and most preferably at least 50 contiguous amino acids of a HIO protein. Functional domains of HIO genes are listed in column 6 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length HIO polypeptides, or fragments thereof, include polypeptides with amino acid insertions, deletions, or substitutions that retain one or more of the biological properties associated with the full-length HIO polypeptide. In some cases, variants are generated that change the post-translational processing of an HIO polypeptide. For instance, variants may have altered protein transport or protein localization characteristics, or altered protein half-life, compared to the native polypeptide.

As used herein, the term "HIO nucleic acid" refers to any polynucleotide that when expressed in a plant causes an altered phenotype in any part of the plant, for example the seeds. In one embodiment, a HIO polynucleotide encompasses nucleic acids with the sequence provided in or complementary to the GenBank entry referenced in column 3 of Tables 2 and 3, which correspond to nucleic acid sequences set forth as SEQ ID NO: 1, SEQ ID NO: 3, SEQ ID NO: 5, or SEQ ID NO: 7, as well as functionally active fragments, derivatives, or orthologs or paralogs thereof. A HIO nucleic acid of this disclosure may be DNA, derived from genomic DNA or cDNA, or RNA.

In one embodiment, a functionally active HIO nucleic acid encodes or is complementary to a nucleic acid that encodes a functionally active HIO polypeptide. A functionally active HIO nucleic acid also includes genomic DNA that serves as a template for a primary RNA transcript (i.e., an mRNA precursor) that requires processing, such as splicing, before encoding the functionally active HIO polypeptide. A HIO nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO polypeptide, or an intermediate form. A HIO polynucleotide can also include heterologous coding sequences, for example, sequences that encode a marker included to facilitate the purification of the fused polypeptide, or a transformation marker. In another embodiment, a functionally active HIO nucleic acid is capable of being used in the generation of loss-of-function HIO phenotypes, for instance, via antisense suppression, co-suppression, etc. The disclosure also provides feed, meal, grain, food, or seed comprising a nucleic acid sequence that encodes an HIO polypeptide.

In one preferred embodiment, a HIO nucleic acid used in the disclosed methods comprises a nucleic acid sequence that encodes, or is complementary to a sequence that encodes, a HIO polypeptide having at least 50%, 60%, 70%, 75%, 80%, 85%, 90%, 95%, 97%, 98%, or 99% sequence identity to a disclosed HIO polypeptide sequence, for example the amino acid sequence set forth as SEQ ID NO: 2, SEQ ID NO: 4, SEQ ID NO: 6, or SEQ ID NO: 8.

In another embodiment, a HIO polypeptide comprises a polypeptide sequence with at least 50% or 60% identity to a disclosed HIO polypeptide sequence (for example, the amino acid sequence set forth as SEQ ID NO: 2, SEQ ID NO: 4, SEQ ID NO: 6, or SEQ ID NO: 8,) and may have at least 70%, 80%, 85%, 90%, 95%, 97%, 98%, or 99% sequence identity to a disclosed HIO polypeptide sequence. In a further embodiment, a HIO polypeptide comprises 50%, 60%, 70%, 80%, 85%, 90%, 95%, 97%, 98%, or 99% sequence identity to a disclosed HIO polypeptide sequence, and may include a conserved protein domain of the HIO polypeptide (such as the protein domain(s) listed in column 6 of Table 2). In another embodiment, a HIO polypeptide comprises a polypeptide sequence with at least 50%, 60%, 70%, 80%, 85%, 90%, 95%, 97%, 98%, or 99% sequence identity to a functionally active fragment of the polypeptide referenced in column 4 of Table 2. In yet another embodiment, a HIO polypeptide comprises a polypeptide sequence with at least 50%, 60%, 70%, 80%, 90%, 95%, 97%, 98%, or 99% identity to the polypeptide sequence of the GenBank entry referenced in column 4 of Table 2 over its entire length and comprises a conserved protein domain(s) listed in column 6 of Table 2.

In another aspect, a HIO polynucleotide sequence is at least 50% to 60% identical over its entire length to a disclosed HIO nucleic acid sequence, such as the nucleic acid sequence set forth as SEQ ID NO: 1, SEQ ID NO: 3, SEQ ID NO: 5, or SEQ ID NO: 7, or nucleic acid sequences that are complementary to such a HIO sequence, and may comprise at least 70%, 80%, 85%, 90%, 95%, 97%, 98%, or 99% sequence identity to the disclosed HIO sequence, or a functionally active fragment thereof, or complementary sequences. In another embodiment, a disclosed HIO nucleic acid comprises a nucleic acid sequence as shown in SEQ ID NO: 1, SEQ ID NO: 3, SEQ ID NO: 5, or SEQ ID NO: 7, or nucleic acid sequences that are complementary to such a HIO sequence, and nucleic acid sequences that have substantial sequence homology to a such HIO sequences. As used herein, the phrase "substantial sequence homology" refers to those nucleic acid sequences that have slight or inconsequential sequence variations from such HIO sequences, i.e., the sequences function in substantially the same manner and encode an HIO polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.*, 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed HIO nucleic acid sequences (for example, the nucleic acid sequence set forth as SEQ ID NO: 1, SEQ ID NO: 3, SEQ ID NO: 5, or SEQ ID NO: 7). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.,).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1× SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6× SSC, 1× Denhardt's solution, 100 µg/ml yeast tRNA and 0.05% sodium pyrophosphate; and washing of filters at 65° C. for 1 h in a solution containing 0.1× SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5× SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2× SSC and 0.1% SDS. Alternatively, low stringency conditions can be used that comprise: incubation for 8 hours to overnight at 37° C. in a solution comprising 20% formamide, 5× SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs (and/or paralogs) of a disclosed *Arabidopsis* HIO nucleic acid sequence. Representative putative orthologs (and/or paralogs) of each of the disclosed *Arabidopsis* HIO genes are identified in column 5 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.*, 95:5849-5856; Huynen M A et al., 2000, *Genome Research*, 10:1204-1210).

Programs for multiple sequence alignment, such as CLUSTAL (Thompson J D et al., 1994, *Nucleic Acids Res.* 22:4673-4680) may be used to highlight conserved regions and/or residues of homologous (orthologous and/or paralogous) proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual,* Cold Spring Harbor Laboratory Press, NY). For instance, methods for generating a cDNA library from the plant species of interest and probing the library with partially homologous gene probes are described in Sambrook et al. A highly conserved portion of the *Arabidopsis* HIO coding sequence may be used as a probe. HIO ortholog nucleic acids may hybridize to the nucleic acid of SEQ ID NO: 1, SEQ ID NO: 3, SEQ ID NO: 5, or SEQ ID NO: 7, under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known HIO polypeptides are used for ortholog (and/or paralog) isolation (see, e.g., Harlow and Lane, 1988, 1999, *Antibodies: A Laboratory Manual*, Cold Spring Harbor Laboratory Press, New York). Western blot analysis can determine that a HIO ortholog (i.e., a protein orthologous to a disclosed HIO polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO nucleic acid and/or polypeptide sequences have been identified.

HIO nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel TA et al., 1991, *Methods Enzymol.* 204:125-39), may be used to introduce desired changes into a cloned nucleic acid.

In general, the methods disclosed herein involve incorporating the desired form of the HIO nucleic acid into a plant expression vector for transformation of plant cells, and the HIO polypeptide is expressed in the host plant. Transformed plants and plant cells expressing an HIO polypeptide express an altered phenotype and, in one specific, non-limiting example, may have high (increased) oil, high (increased) protein, and/or low (decreased) fiber content.

An "isolated" HIO nucleic acid molecule is other than in the form or setting in which it is found in nature, and is identified and separated from least one contaminant nucleic acid molecule with which it is ordinarily associated in the natural source of the HIO nucleic acid. However, an isolated HIO nucleic acid molecule includes HIO nucleic acid molecules contained in cells that ordinarily express the HIO polypeptide where, for example, the nucleic acid molecule is in a chromosomal location different from that of natural cells.

Generation of Genetically Modified Plants with an Altered Phenotype

The disclosed HIO nucleic acids and polypeptides may be used in the generation of transgenic plants having a modified or altered phenotype, for example an altered oil, protein, and/or fiber content phenotype. As used herein, an "altered oil content (phenotype)" may refer to altered oil content in any part of the plant. In a preferred embodiment, altered expression of the HIO gene in a plant is used to generate plants with a high oil content (phenotype). As used herein, an "altered total protein content (phenotype)" or an "altered digestible protein content (phenotype)" may refer to altered protein (total or digestible) content in any part of the plant. In a preferred embodiment, altered expression of the HIO gene in a plant is used to generate plants with a high (or increased) total or digestible protein content (phenotype). As used herein, an "altered fiber content (phenotype)" may refer to altered fiber content in any part of the plant. In a preferred embodiment, altered expression of the HIO gene in a plant is used to generate plants with a low (or decreased) fiber content (phenotype). The altered oil, protein and/or fiber content is often observed in seeds. Examples of a transgenic plant include plants comprising a plant transformation vector with a nucleotide sequence that encodes or is complementary to a sequence that encodes an HIO polypeptide having the amino acid sequence as set forth in SEQ ID NO: 2, SEQ ID NO: 4, SEQ ID NO: 6, or SEQ ID NO: 8, or an ortholog or paralog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the HIO nucleic acid sequence (or an ortholog, paralog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (Medicago sativa), tobacco (Nicotiana), turfgrass (Poaceae family), other forage crops, and wild species may also be a source of unique fatty acids. In other embodiments, any plant expressing the HIO nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.*, 91:694-701), maize (Ishida et al., 1996 *Nature Biotechnol.* 14:745-750, Zhang et al., 2002 *Plant Cell Rep.* 21:263-270) sunflower (Everett et al., 1987, *Bio/Technology*, 5:1201), soybean (Christou et al., 1989, *Proc. Natl. Acad. Sci USA*, 86:7500-7504; Kline et al., 1987, *Nature*, 327:70), wheat, rice and oat.

Expression (including transcription and translation) of a HIO nucleic acid sequence may be regulated with respect to the level of expression, the tissue type(s) where expression takes place and/or developmental stage of expression. A number of heterologous regulatory sequences (e.g., promoters and enhancers) are available for controlling the expression of a HIO nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (U.S.A) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.*, 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (U.S.A.) 84:6624-6628, 1987), the sucrose synthase promoter (Yang et al., *Proc. Natl. Acad. Sci.* (U.S.A.) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol Biol.*, 37:1055-1067), and the melon actin promoter (published PCT application WO0056863). Exemplary tissue-specific promoters include the tomato E4 and E8 promoters (U.S. Pat. No. 5,859,330 and the tomato 2AII gene promoter (Van Haaren M J J et al., 1993, *Plant Mol Bio.*, 21:625-640).

In one preferred embodiment, expression of the HIO nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209: 219, 1991), globulin (Belanger and Kriz, *Genet.*, 129: 863-872, 1991, GenBank Accession No. L22295), gamma zein Z27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (U.S. Application No. 2003/0046727), a soybean 7S promoter, a 7Sα' promoter (U.S. Application No. 2003/0093828), the soybean 7Sα' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mot. Biol.*, 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., Plant Mol. Biol., 34(3):549-555, 1997). Also included are the zeins, which are a group of storage proteins found in corn endosperm. Genomic clones for zein genes have been isolated (Pedersen et al., *Cell*, 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba legumin* (Baumlein et al., 1991, *Mol. Gen. Genet.* 225:121-8; Baumlein et al., 1992, *Plant J.* 2:233-9), *V. faba usp* (Fiedler et al., 1993, *Plant Mol. Biol.* 22:669-79), pea convicilin (Bown et al., 1988, *Biochem. J.* 251:717-26), pea lectin (depater et al., 1993, *Plant Cell* 5:877-86), *P. vulgaris beta phaseolin* (Bustos et al., 1991, *EMBO J.* 10: 1469-79), *P. vulgaris* DLEC2 and PHS [beta] (Bobb et al., 1997, *Nucleic Acids Res.* 25:641-7), and soybean beta-*Conglycinin*, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus napin*, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus oleosin* (Keddie et al., 1994, *Plant Mol. Biol.* 24:327-40), *Arabidopsis oleosin* (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378, 619; 5,391,725; 5,428,147; 5,447,858; 5,608,144; 5,608,144; 5,614,399; 5,633,441; 5,633,435; and 4,633,436.

In another embodiment, the endogenous HIO gene may be placed under the control of a transgenic transcription factor or used to design binding sites that modulates its expression. One such class of transcription factors are the $Cys_2$-$His_2$-zinc finger proteins (ZFPs). ZFPs are common DNA binding proteins and can be designed to specifically bind to specific DNA sequences (Beerli & Barbas, Nat Biotechnol., 2002, 20:135-141.;Gommans et al., J Mol Biol., 2005, 354:507-519). Individual zinc-finger domains are composed of approximately 30 amino acids, are structurally conserved and can interact with 3-4 bp of DNA. A polypeptide containing multiple zinc-fingers designed to bind to a specific DNA sequence in the promoter of a HIO gene can be synthesized. The principles for designing the zinc finger domains to interact with specific DNA sequences have been described in Segal et al, (Segal et al., Proc Natl Acad Sci U S A., 1999, 96:2758-2763), Dreier et al. (Dreier et al., J Mol Biol., 2000, 303:489-502), and Beerli and Barbas (Beerli & Barbas, Nat Biotechnol., 2002, 20:135-141). These DNA binding domains may be fused to effector domains to form a synthetic ZFP that may regulate transcription of genes to which they bind. Effector domains that can activate transcription include but are not limited to the acidic portion of the herpes simplex virus protein VP16 (Sadowski et al., Nature., 1988, 335:563-564) and VP64 (Beerli et al., Proc Natl Acad Sci U S A., 1998, 95:14628-14633), and the NF-κB transcription factor p65 domain (Bae et al., Nat Biotechnol., 2003, 21:275-280., Liu et al., J Biol Chem., 2001, 276:11323-11334). Effector domains that can repress transcription include but are not limited to mSIN3 and KRAB (Ayer et al., Mol Cell Biol., 1996, 16:5772-5781, Beerli & Barbas, Nat Biotechnol., 2002, 20:135-141, Beerli et al., Proc Natl Acad Sci U S A, 1998, 95:14628-14633, Margolin et al., Proc Natl Acad Sci U S A., 1994, 91:4509-4513). These approaches have been shown to work in plants (Guan et al., Proc Natl Acad Sci U S A., 2002, 99:13296-13301, Stege et al., Plant J., 2002, 32:1077-1086, Van Eenennaam et al., Metab Eng., 2004, 6:101-108).

In yet another aspect, in some cases it may be desirable to inhibit the expression of the endogenous HIO nucleic acid sequence in a host cell. Exemplary methods for practicing this aspect of the invention include, but are not limited to antisense suppression (Smith, et al., 1988, Nature, 334:724-726; van der Krol et al., 1988, BioTechniques, 6:958-976); co-suppression (Napoli, et al., 1990, Plant Cell, 2:279-289); ribozymes (PCT Publication WO 97/10328); and combinations of sense and antisense (Waterhouse, et al., 1998, Proc. Natl. Acad. Sci. USA, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, Proc. Natl. Acad. Sci. USA, 85:8805-8809), a partial cDNA sequence including fragments of 5' coding sequence, (Cannon et al., 1990, Plant Mol. Biol., 15:39-47), or 3' non-coding sequences (Ch'ng et al., 1989, Proc. Natl. Acad. Sci. USA, 86:10006-10010). Cosuppression techniques may use the entire cDNA sequence (Napoli et al., 1990, Plant Cell, 2:279-289; van der Krol et al., 1990, Plant Cell, 2:291-299), or a partial cDNA sequence (Smith et al., 1990, Mol. Gen. Genetics, 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, Arch. Virol. Suppl. 15:189-201).

In a preferred application expression profiling, generally by microarray analysis, is used to simultaneously measure differences or induced changes in the expression of many different genes. techniques for microarray analysis are well known in the art (Schena M et al., Science 1995 270:467-470; Baldwin D et al., 1999, Cur. Opin. Plant Biol. 2(2):96-103; Dangond F, Physiol Genomics (2000) 2:53-58; van Hal NL et al., J Biotechnol. (2000) 78:271-280; Richmond T and Somerville S, Curr. Opin. Plant Biol. 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Phenotype

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen (such as ethylmethane sulfonate, methyl methane sulfonate, diethylsulfate, and nitrosoguanidine, or 5-bromo-deoxyuridine) radiation, or ultraviolet light. In some embodiments of the method, the mutated plant can be bred to generate progeny, which inherit the mutation or allele and have an altered phenotype. For example, provided herein is a method of identifying plants that have one or more mutations in the endogenous HIO nucleic acid sequence that confer an altered phenotype and generating progeny of these mutated plants having such a phenotype that are not transgenic. The mutated plants with an altered phenotype can have an altered oil, protein, and/or fiber content, or an altered seed meal content.

In one specific embodiment of the method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the HIO nucleic acid sequence is used to identify whether a mutated plant has a mutation in the HIO nucleic acid sequence. Plants having HIO mutations may then be tested for altered oil, protein, and/or fiber content. To confirm that the HIO mutation causes the modified phenotype, experiments correlating the presence of the modified gene and the modified phenotype through genetic crosses can be performed. TILLING can identify mutations that alter the expression of specific genes or the activity of proteins encoded by these genes (see Colbert et al., 2001, Plant Physiol. 126:480-484; McCallum et al., 2000, Nature Biotechnology 18:455-457).

In another specific embodiment of the method, a candidate gene/Quantitative Trait Locus (QTLs) approach can be used in a marker-assisted breeding program to identify alleles of or mutations in the HIO nucleic acid sequence or orthologs (and/or paralogs) of the HIO nucleic acid sequence that may confer altered oil, protein, and/or fiber content (see Bert et al., Theor Appl Genet., 2003 June; 107(1):181-9; and Lionneton et al., Genome, 2002 December;45(6):1203-15). Thus, in a further aspect of the disclosure, a HIO nucleic acid is used to identify whether a plant having altered oil, protein, and/or fiber content has a mutation in an endogenous HIO nucleic acid sequence or has a particular allele that causes altered oil, protein, and/or fiber content in the plant.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with a HIO Phenotype by Transformation with an Activation Tagging Construct This Example describes the generation of transgenic plants with altered oil, protein, and/or fiber content.

Mutants were generated using the activation tagging "ACTTAG" vector, pSKI015 (GI#6537289; Weigel D et al., 2000, *Plant Physiology*, 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4X CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR total protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A NIR fiber content predicting calibration was developed using crude fiber content data of seed samples following the general method of AOAC Official Method 962.09 (Official Methods of Analysis of AOAC International 17$^{th}$ Edition AOAC, Gaithersburg, Md.). A NIR oleic acid content predicting calibration was developed using oleic acid content data of seed samples determined by following the method of Browse et al. (1986 Anal. Biochem. 152:141-145). A NIR calibration curve for predicting digestible protein content was developed by measuring digestible protein content in a set of seed samples. Total protein content of in a known mass of seed was determined by measuring the total nitrogen content of the seed using the Dumas method (AOAC Official Method 968.06). The seed fiber is extracted from a separate seed sample using the method of Honig and Rackis, (1979, *J. Agri. Food Chem.*, 27: 1262-1266). The undigested protein remaining associated with the fiber is measured by the Dumas method (AOAC Official Method 968.06). Digestible protein content is determined by subtracting the amount of undigested protein associated with the fiber from the total amount of protein in the seed.

Oil, protein and fiber predictions from NIR spectra were compared for 82,274 individual ACTTAG lines. Subsequent to seed compositional analysis, the position of the ACTTAG element in the genome in each line was determined by inverse PCR and sequencing. 37,995 lines with recovered flanking sequences were considered in this analysis.

Seed oil, and protein values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Generally, promoters within 9 kb of the enhancers in the ACTTAG element are considered to be within "activation space." Genes with T-DNA inserts within coding sequences were not considered to be within "activation space." The ACTTAG lines identified are listed in column 3 of Table 1. In some cases more than one ACTTAG line is associated with a gene. The relative oil, protein, fiber and oleic acid values in columns 4, 5, 6 and 7, respectively, are determined by comparing the seed component in the plant identified in column 3 relative to other plants grown at the same time and not displaying the trait.

TABLE 1

| 1. Alias | 2. TAIR ID | 3. Plant ID | 4. Relative Oil (%) | 5. Relative Protein (%) | 6. Relative Fiber (%) | 7. Relative Oleic Acid |
|---|---|---|---|---|---|---|
| HIO2040 B | At1g59030 | IN054699 | 108.27 | 92.54 | 112.4 | 91.54 |
| HIO2040 B | At1g59030 | IN018508 | 106.7 | 95.18 | 96.58 | 101.4 |
| HIO2049 B | At1g78390 | IN088881 | 120.77 | 81.56 | 102.39 | 175.77 |
| HIO2049 B | At1g78390 | IN087017 | 110.07 | 94.94 | 94.37 | 127.81 |
| HIO2094 A | At3g13220 | IN090531 | 128.14 | 75.88 | 117.6 | |
| HIO2094 A | At3g13220 | IN041823 | 108.28 | 98.85 | 97.35 | 102.03 |

TABLE 2

| 1. Locus | 2. Tair ID | 3. Nucleic Acid seq. GI# | 4. Poly-peptide seq. GI# | 5. Putative biochemical function/ protein name | 6. Conserved protein domain |
|---|---|---|---|---|---|
| HIO2040 B | At1g59030 | GI:18406326 | GI:18406327 | GDSL-motif lipase, putative | IPR001087 Lipolytic enzyme, G-D-S-L |
| HIO2040 B | At1g59030 | gi\|79366432 | gi\|79366433 | carboxylic ester hydrolase/lipase | IPR001087 Lipolytic enzyme, G-D-S-L |
| HIO2049 B | At1g78390 | gi\|30699326 | gi\|15218314 | 9-cis-epoxycarotenoid dioxygenase, putative/ neoxanthin cleavage enzy | IPR004294 Retinal pigment epithelial membrane protein |
| HIO2094 A | At3g13220 | gi\|22331044 | gi\|22331045 | ABC transporter family protein | IPR005895 Heme exporter protein CcmA IPR003593 AAA ATPase IPR003439 ABC transporter related IPR000412 ABC-2 IPR005892 Glycine betaine/L-proline transport ATP-binding Subunit IPR005876 Cobalt transport protein ATP-binding subunit IPR005942 Daunorubicin resistance ABC transporter membrane protein IPR005666 Sulphate transport system permease protein 1 IPR005968 Thiamine ABC transporter, ATP-binding protein |

TABLE 3

| | | | | 5. Orthologs | | |
|---|---|---|---|---|---|---|
| 1. Locus | 2. Tair ID | 3. Nucleic Acid seq. GI# | 4. Poly-peptide seq. GI# | Nucleic Acid GI# | Polypeptide GI# | Species |
| HIO2040 B | At1g59030 | GI:18406326 | GI:18406327 | gi\|18406354 | gi\|18406355 | *Arabidopsis thaliana* |
| | | | | GI:18406326 | GI:18406327 | *Arabidopsis thaliana* |
| | | | | gi\|18407592 | gi\|15229719 | *Arabidopsis thaliana* |
| | | | | gi\|42565423 | gi\|42565424 | *Arabidopsis thaliana* |
| HIO2040 B | At1g59030 | gi\|79366432 | gi\|79366433 | gi\|42565423 | gi\|42565424 | *Arabidopsis thaliana* |
| | | | | gi\|18406312 | gi\|15217977 | *Arabidopsis thaliana* |
| | | | | gi\|22330311 | gi\|22330312 | *Arabidopsis thaliana* |
| | | | | gi\|18407592 | gi\|15229719 | *Arabidopsis thaliana* |
| HIO2049 B | At1g78390 | gi\|30699326 | gi\|15218314 | gi\|30683162 | gi\|15231856 | *Arabidopsis thaliana* |
| | | | | gi\|28974076 | gi\|28974077 | *Lycopersicon esculentum* |
| | | | | gi\|50346888 | gi\|50346889 | *Solanum tuberosum* |
| HIO2094 A | At3g13220 | gi\|22331044 | gi\|22331045 | gi\|30681494 | gi\|18415230 | *Arabidopsis thaliana* |
| | | | | gi\|42565857 | gi\|15231177 | *Arabidopsis thaliana* |
| | | | | gi\|51091372 | gi\|51091387 | *Oryza sativa* (*japonica* cultivar-group) |

Example 2

Analysis of the *Arabidopsis* HIO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318), PSORT (Nakai K, and Horton P, 1999, *Trends Biochem. Sci.* 24:34-6), and/or CLUSTAL (Thompson J D et al., 1994, *Nucleic Acids Res.* 22:4673-4680).

Example 3

Recapitulation Experiments

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into Arabidopsis plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value≦0.05. These constructs are listed in Table 4. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

TABLE 4

| | | | ANOVA | | | | Average 10. | | | |
|---|---|---|---|---|---|---|---|---|---|---|
| 1. Alias | 2. Tair | 3. Construct | 4. Protein | 5. Oil | 6. Digestible Protein | 7. Fiber | 8. Protein | 9. Oil | Digestible Protein | 11. Fiber |
| HIO2040 B | At1g59030 | CsVMV::At1g59030 | 0.137 | 0.028 | <.0001 | <.0001 | 102.8% | 103.2% | 105.6% | 93.2% |
| HIO2040 B | At1g59030 | Pru::At1g59030 | 0.683 | 0.130 | 0.099 | 0.015 | 100.9% | 101.8% | 101.7% | 97.6% |
| HIO2049 B | At1g78390 | CsVMV::At1g78390 | 0.909 | 0.773 | 0.378 | 0.666 | 99.9% | 100.5% | 100.9% | 99.4% |
| HIO2049 B | At1g78390 | Pru::At1g78390 | 0.306 | 0.013 | <.0001 | <.0001 | 101.1% | 102.6% | 103.0% | 95.9% |
| HIO2094 A | At3g13220 | CsVMV::At3g13220 | 0.855 | 0.014 | 0.011 | 0.001 | 99.7% | 103.2% | 102.5% | 96.3% |
| HIO2094 A | At3g13220 | Pru::At3g13220 | 0.093 | 0.282 | 0.001 | 0.001 | 102.6% | 100.9% | 103.0% | 97.4% |

It is claimed:

1. A method of generating a plant having an increased oil content, comprising:

identifying a plant that has an allele in its ortholog of the *A. thaliana* HIO2094A gene, where the wild-type *A. thaliana* HIO2094A gene has the nucleic acid sequence set forth as SEQ ID NO: 7, which allele results in increased oil content compared to plants lacking the allele; and generating progeny of said identified plant, wherein the generated progeny inherit the allele and have the high oil phenotype.

2. The method of claim 1 that employs candidate gene/QTL methodology.

3. The method of claim 1 that employs TILLING methodology.

4. A method of generating a plant having an improved meal quality phenotype comprising:

identifying a plant that has an allele in its ortholog of the *A. thaliana* HIO2094A gene, where the wild-type *A. thaliana* HIO2094A gene has the nucleic acid sequence set forth as SEQ ID NO: 7, which allele results in increased meal quality compared to plants lacking the allele; and generating progeny of said identified plant, wherein the generated progeny inherit the allele and have the increased meal quality, thereby generating a plant having an improved meal quality phenotype.

5. The method of claim 4 that employs candidate gene/QTL methodology.

6. The method of claim 4 that employs TILLING methodology.

* * * * *